(12) United States Patent
Khan et al.

(10) Patent No.: US 7,497,983 B2
(45) Date of Patent: Mar. 3, 2009

(54) COLORING OF CERAMICS BY ATMOSPHERE CONTROL

(75) Inventors: Ajmal Khan, Princeton, NJ (US); Dmitri G. Brodkin, Livingston, NJ (US)

(73) Assignee: Pentron Ceramics, Inc., Somerset, NJ (US)

( * ) Notice: Subject to any disclaimer, the term of this patent is extended or adjusted under 35 U.S.C. 154(b) by 0 days.

(21) Appl. No.: 11/889,945

(22) Filed: Aug. 17, 2007

(65) Prior Publication Data
US 2008/0085828 A1    Apr. 10, 2008

Related U.S. Application Data

(60) Provisional application No. 60/838,375, filed on Aug. 18, 2006.

(51) Int. Cl.
*A61C 13/20* (2006.01)

(52) U.S. Cl. .................. 264/673; 264/671; 264/17

(58) Field of Classification Search .............. 264/17, 264/671, 673, 20
See application file for complete search history.

(56) References Cited

U.S. PATENT DOCUMENTS

| | | | | | |
|---|---|---|---|---|---|
| 4,647,414 | A | * | 3/1987 | Mizuno et al. | 264/667 |
| 6,106,747 | A | * | 8/2000 | Wohlwend | 264/16 |

* cited by examiner

*Primary Examiner*—Steven P Griffin
*Assistant Examiner*—Russell J Kemmerle, III
(74) *Attorney, Agent, or Firm*—George R. McGuire; Ann M. Knab; Bond Schoeneck & King, PLLC (57) ABSTRACT

Methods of forming a colored ceramic body or dental article are described that include: (a) forming a body from a ceramic-containing powder; (b) shaping the body into a desired shape; and (c) firing the shaped body in an atmosphere comprising at least one coloring agent. Methods of forming a fully dense ceramic body that lacks discoloration, are also described which include: (a) forming a body from a ceramic-containing powder; (b) shaping the body into a desired shape; (c) placing the shaped body in a firing atmosphere containing at least one impurity that promote discoloration of the ceramic body; (d) placing the ceramic body in proximity to an atmosphere powder; and (e) firing the shaped body in proximity to an atmosphere powder; wherein the atmosphere powder acts as at least one of a barrier and a getter for the at least one impurity.

65 Claims, 1 Drawing Sheet

COLORING OF CERAMICS BY ATMOSPHERE CONTROL

The present application claims priority, pursuant to 35 U.S.C. §119, to provisional U.S. patent application Ser. No. 60/838,375 filed Aug. 18, 2006, the entire contents of which is incorporated herein by reference.

FIELD OF THE INVENTION

The present invention is directed to techniques and arrangements useful for coloring ceramic materials. According to certain aspects, the present invention is directed to techniques and arrangements useful for coloring dental ceramic materials. The present invention is also directed to techniques and arrangements useful for stabilizing the color of an as-fired ceramic, and/or preventing discoloration thereof.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Ceramics such as zirconia-based materials have emerged as high-strength framework materials for dental prostheses (single-units up to multiple unit bridges). However, such materials are often an intense white color, and consequently the esthetics of the finished restoration is unacceptable in its natural color.

A finished dental restoration should match the color of the patient's teeth, i.e., it should be "tooth colored". The colors of human teeth appear to range from a light almost white-tan to a light brown, and occupy a very specific color space. This color space can be described by the commonly used CIE (Commission Internationale de l'Eclariage) L*, a*, b* conventions, which represents colors in a three-dimensional Cartesian coordinate system. L*, or "value," is a measure of luminance or lightness, and is represented on the vertical axis. The a*, b* coordinates, are a measure of chromaticity and are represented on horizontal coordinates, with positive a* representing red, a negative a* representing green, a positive b* representing yellow, and negative b* representing blue. U.S. Pat. No. 6,030,209, which is incorporated herein by reference, presents the CIE L*, a*, b* color coordinates of tooth colors represented by the Vita Lumen® shade guide system manufactured by Vita Zahnfabrik (i.e., it presents the color space of tooth colors). As used herein, "tooth color" or "tooth-like color" is taken to mean CIE L*, a*, b* color coordinates that fall within, or very close to, this color space.

Currently there are two main commercially available methods to deal with the stark white color of dental ceramics such as zirconia. In the one method, the white ceramic is "hidden" by applying either a layer of stain or a liner to a sintered framework. The other method entails shading the ceramic by immersion in, or painting with, coloring solutions while in the pre-sintered state. Coloring with stain/liner is undesirable as it is an extra fabrication step and because it lowers translucency. Shading with a coloring solution is undesirable because it requires the extra step of dipping or painting, and extra time to dry before sintering.

U.S. Pat. No. 6,713,421 appears to describe pre-sintered zirconia blanks that are colored with 0.2-1.5 wt. % coloring additives, selected from the group consisting of the oxides $Fe_2O_3$, $Er_2O_3$ and $MnO_2$. The blanks are intended for CAD/CAM processing into dentures. French patent publication 2,787,366 and Cales et. al. ("Colored Zirconia Ceramics for Dental Applications," Bioceramics Vol. 11, edited by R. Z. LeGeros and J. R. LeGeros; Proceedings of the 11th International Symposium on Ceramics in Medicine; York, N.Y.; November 1998) appear to identify a number of colorants, and was reportedly successful in achieving some of the Vita shades by using combinations of $Fe_2O_3$, $CeO_2$ and $Bi_2O_3$. Bushan et al. (S. Bushan, R. Pober and R. Giordano, "Coloration of Partially Stabilized Zirconia," Abstract 1775, Journal of Dental Research, Vol. 84, Special Issue A, 2005) appears to describe the study of the coloration of partially stabilized zirconia by a variety of solutions comprising coloring cations. U.S. Pat. No. 5,219,805 appears to disclose coloration of stabilized zirconia for dental bracket applications using combinations of $Fe_2O_3$, $Er_2O_3$, and $Pr_6O_{11}$. U.S. Pat. No. 5,656,564 appears to describe coloration of zirconia with combinations of $Er_2O_3$ and $Pr_6O_{11}$. U.S. Pat. No. 5,011,403 appears to describe coloration of zirconia using combinations of Fe, Ni and Mn in the form of water solutions of sulfates and acetates, respectively, added to a ceramic slip. U.S. Pat. No. 6,709,694 appears to describe the use solutions for coloring of pre-sintered zirconia by immersion, painting or spraying using a metal ion coloring solution or metal complex coloring solution that is applied to a presintered ceramic, followed by sintering to form a translucent, colored dental ceramic. The ions or complexes are of the rare earths elements or subgroups II and VIII, with an action time of less than two hours, and maximum pre-sintered zirconia diameter and height of 10 and 7 mm, respectively. All of the above identified documents are incorporated by reference herein in their entirety The coloring of technical zirconias is also documented. For example, the development of pink coloration in zirconia by Er additions is described in: (i) P. Duran, P. Recio, J. R. Jurado, C. Pascual and C. Moure, "Preparation, Sintering, and Properties of Translucent $Er_2O_3$-Doped Tetragonal Zirconia," J. Am. Ceram. Soc., vol. 72, no. 11, pp. 2088-93, 1989; and (ii) M. Yashima, T. Nagotome, T. Noma, N. Ishizawa, Y. Suzuki and M. Yoshimura, "Effect of Dopant Species on Tetragonal (t')-to-Monoclinic Phase Transformation of Arc-Melted $ZrO_2$—$RO_{1.5}$ (R=Sm, Y, Er, and Sc) in Water at 200° C. and 100 MPa Pressure," J. Am. Ceram. Soc., no. 78, no. 8, pp. 2229-93, 1989. Additions of CoO, $Fe_2O_3$ and $Cr_2O_3$ combinations to yttria-stabilized zirconia are known to impart a blue color in the final sintered zirconia bodies, as apparently described in Japanese patent publication 2,145,475. Additions of NiO and $Cr_2O_3$ to yttria-stabilized zirconia have been shown to result in a purplish colored sintered body, as apparently described in Japanese patent publication 5,043,316. All of the above identified documents are incorporated by reference herein in their entirety.

Most of the aforementioned coloring additions can negatively affect not only mechanical properties, including strength and fracture toughness, but also isotropic shrinkage and final sintered density. This can happen for a number of reasons including: (1) loss of fracture toughness from a lowering of the "transformation toughening" effect as a result of the over-stabilization of the tetragonal phase by the additive (either chemically, or by grain size reduction) thereby hindering the transformation from the metastable tetragonal phase to monoclinic phase that is necessary for the toughening to happen; (2) loss of strength due to spontaneous microcrack formation that can result if grains grow too large because of the coloring additive; and (3) loss of strength due to the formation of strength-limiting pores in the microstructure due to the coloring additive. This last reason is what Shah et al. (K. C. Shah, I. Denry and J. A. Holloway, "Physical Properties of Cerium-Doped Tetragonal Zirconia," Abstract 0080, Journal of Dental Research, Vol. 85, Special Issue A, 2006) attribute the significant loss of strength, down to 275±67 MPa, for 3YTZP materials that were colored using Ce salts. The problem of formation of larger pores, along with grain growth, in colored zirconia sintered compacts has also been recently recognized by Omichi and Takei (N. Omichi and T. Takei, "Colored Zirconia Sintered Compact and its Production Process," JP 2005289721, Oct. 20, 2005).

Thus, it would be beneficial to provide ceramic materials with a desired coloring without resorting to extra processing steps such as required for the staining/liner or coloring by solutions (liquids) techniques, and without any significant compromise of physical properties of the resulting densified ceramic material.

Often times, the color of an as-sintered ceramic materials may exhibit instability when subjected to certain conditions or environments. For example, the color of as-sintered zirconia frameworks may not be stable when subjected to the subsequent firings which are necessary to overlay the framework with porcelain to produce a finished restoration. Typically, an overlay porcelain for zirconia frameworks is fired, or pressed, under vacuum at levels of approximately 35 torr at temperatures of 750-1065° C. These conditions are reducing relative to the atmosphere in which the zirconia is sintered. Since the color of zirconia can be affected by exposure to reducing conditions as illustrated, for example, by Romer et al. (H. Romer, K.-D. Luther and W. Asmus, "Colored Zirconia," Cryst. Res. Technol., 29, 6, 787-794 (1994)), the color of the framework may not be stable. For example, Romer et al. documented the following color transitions for 12 mol % yttria stabilized zirconia crystals colored with various dopants upon exposure to oxidizing versus reducing conditions at 1100° C.: yellow to red-brown for vanadium, green to brown for chromium, violet to pale orange for manganese, green to yellow for iron, violet to violet-blue for cobalt, and colorless to yellow for nickel. It is understood that the underlying reason for the change in color is the change in the thermodynamic oxygen vacancy concentration of the zirconia, as dictated in part by the oxygen potential of the firing atmosphere. Due to charge compensation reasons, this can effect a change in the valence of the coloring dopant, and thus change the color of the zirconia. The effect can be especially rapid in zirconia due to an inherently high oxygen diffusivity. During the porcelain overlaying steps the inside of a restoration is exposed, it is thus susceptible to changes in color due to the vacuum firing conditions. Additionally, the oxygen potential of the porcelain, which is expected to be different than that of air, can also contribute to color change for the same reason. It is speculated that the change in the zirconia oxygen vacancy concentration effects a change in color due to a change of the valence of the chromophore ion, for charge compensation, and/or due to a change in the number or oxygen ions coordinated with the chromophore ion.

Thus, it would be extremely beneficial to provide ceramic materials with a coloration that is stable when subjected to certain conditions or environments, such as color stability of dental articles during subsequent processing steps required to produce finished dental restorations.

The propensity for ceramics such as zirconia to become colored by the addition of relatively small amounts of coloring elements can lead to accidental discoloration due to unintended exposure to impurities in the furnace chamber during sintering. The impurities can come from a variety of sources, including the heating elements and kiln furniture, and can build up in the furnace over time. For example, zirconia frameworks will periodically emerge from sintering with yellow discoloration, a problem that is associated with corrosion of molybdenum disilicide heating elements. Consequently, the frameworks, which are supposed to be white, often must be discarded. A solution for this problem has been to run the furnace at a high temperature under good ventilation and with an empty firing sagger several times, which has the effect of regenerating the characteristic protective glassy silica layer on the heating elements, and eliminating the heating element corrosion. It is speculated that the corroded heating elements are the source of an impurity (or impurities), that has a significant enough vapor pressure during the sintering cycle to effect its transport into the zirconia framework and cause yellow discoloration. Although the regeneration of the protective silica layer on the heating elements effectively seals the source of the offending discoloring impurity, and presumably eliminates and or neutralizes it in the furnace lining and furniture thereby permitting for the subsequent sintering of non-discolored frameworks, the operator still unfortunately has to sacrifice some frameworks to get to this point, costing time and money. Regardless of the source of the discoloring impurity or how it gets into the zirconia, it would be useful to have a method to avoid such discoloration.

Thus, it would be would be beneficial to provide a method for sintering ceramic materials, such as white zirconia frameworks, that does not discolor the material with impurities introduced by components or otherwise present in the sintering environment.

Yttria-stabilized zirconia can have lower than desirable hydrolytic resistance, or rather, resistance to hydrolytic degradation, also known as hydrothermal aging or low temperature degradation. Hydrolytic degradation is characterized by the spontaneous transformation of the tetragonal phase into monoclinic upon exposure to water for extended time. It typically occurs at the surface of a densely sintered body after long exposures in warm aqueous environments, and can debit mechanical properties, and is hence undesirable for dental applications. It well known that the addition of aluminum in amounts of 0.1-0.4 wt. % (oxide form, Al2O3) to 3 mol % yttria-stabilized zirconia (3YSZ) will increase hydrolytic resistance. Although there are several commercial alumina doped 3YSZ powders available they are usually more expensive than their alumina-free counterparts. Also, it is possible that the hydrolytic stability of the available alumina doped 3YSZ ceramics can be improved by increasing the alumina content.

Thus, it would be beneficial to provide a method for sintering a ceramic body in a manner that introduces aluminum into the ceramic during sintering.

SUMMARY

The present invention provides techniques and arrangements that can optionally address one or more of the above-mentioned shortcomings associated with conventional technology.

According to one optional aspect of the present invention, ceramic blocks or blanks are provided, which are colored simultaneously with a sintering procedure, and can optionally be processed by CAD/CAM techniques into colored dental frameworks of high strength. This processing may take place prior to the sintering step referenced above. The term "blocks" and "blanks" are not intended to limit the geometry of the articles of the present invention. Any suitable CAD/CAM technique may be utilized in connection with the present invention. For example, such techniques are described in U.S. Pat. No. 7,011,522, the entire contents of which are incorporated herein by reference, in its entirety.

According to one aspect, the present invention provides a method of forming a dental article, the method comprising: (a) forming a body from a ceramic-containing powder; (b) shaping the body into a shape corresponding to the dental article; (c) firing the shaped body in proximity to an atmosphere powder comprising at least one coloring agent.

According to another aspect, the present invention provides a method of forming a fully dense colored ceramic body, the method comprising: (a) forming a body from a ceramic-containing powder; (b) shaping the body into a desired shape; and (c) firing the shaped body in proximity to an atmosphere powder comprising at least one coloring agent.

According to an additional aspect, the present invention provides an atmosphere powder that results in coloration of the as-sintered article that is stable when subjected to certain conditions or environments, such as color stability of dental articles during subsequent processing steps required to produce finished dental restorations.

According to another aspect, the atmosphere powder can be formulated such that it produces an atmosphere during sintering that enhances the hydrolytic stability of the as-fired ceramic.

According to another aspect, the present invention provides an atmosphere powder comprising no coloring agents that acts as a protective barrier against, and/or as a "getter" of coloring impurities in the furnace chamber, thereby preventing unintended discoloration of a ceramic body during sintering.

DETAILED DESCRIPTION

According to certain aspects, the invention provides methods for coloring ceramic materials, such as zirconia dental frameworks, in-situ, during the sintering process. One advantage of this method is that it eliminates steps associated with the coloring by staining/liner or coloring by solutions (liquids) techniques, thereby cutting down on the processing time. Methods of the present invention may entail sintering the ceramic material to be colored in the presence of a ceramic-based atmosphere powder. This atmosphere powder may contain at least one coloring agent. The coloring agent(s) may be present as free or solute element(s), or as a compound(s) of said element(s). The atmosphere powder may also comprise at least one ceramic powder that lacks any coloring agent(s). Any suitable ceramic powder is envisioned. Non-limiting examples of the ceramic powder component of the atmosphere powder include a ceramic oxide powder, yttria and MgO stabilized zirconia powder. The atmosphere powder may also comprise a combination or mixture of different coloring powders. A coloring powder comprises a coloring agent in combination with a ceramic powder. Thus, according to optional embodiments of the present invention, the atmosphere powder comprises a combination of coloring powders that differ at least with respect to the coloring agent(s) they contain. For example, the atmosphere powder may comprise a mixture of at least first and second coloring powders. The first coloring powder comprising a first coloring agent in combination with a first ceramic powder, and the second coloring powder comprising a second coloring agent in combination with a second ceramic powder. The first and second coloring agents differ from each other. The first and second ceramic powders may be the same, or different. The atmosphere powder can comprise a mixture of more than the two coloring powders mentioned above. Moreover, the first and second coloring powders can have coloring agents and/or ceramic powders in addition to the first and second coloring agents and ceramic powders mentioned above.

The at least one coloring agent can be selected from: (a) the lanthanide series of elements and compounds thereof, excluding synthetic and radioactive elements (b) groups 5 to 11 of the periodic table and compounds thereof, excluding synthetic and radioactive elements; and (c) Ti or Sc, and compounds thereof. For the lanthanide series this includes: lanthanum; cerium; praseodymium; neodymium; samarium; europium; gadolinium; terbium; dysprosium; holmium; erbium; thulium; ytterbium; and lutetium. For groups 5 to 11 of the Periodic Table, this includes: vanadium; niobium; tantalum; chromium; molybdenum; tungsten; manganese; rhenium; bohrium; iron; ruthenium; osmium; cobalt; rhodium; iridium; nickel; palladium; platinum; copper; silver; and gold. According to optional embodiments of the present invention, the atmosphere powder may contain a plurality of different coloring agents selected from the above. According to certain embodiments of the present invention, the atmosphere powder is formulated in a manner such that it generates significant vapor pressure of the coloring agent(s) when exposed to elevated temperatures commensurate with firing temperatures used to densify a ceramic body.

The concentration of the at least one coloring agent contained in the atmosphere powder can be provided at any suitable level, for example, 0.0001 to 50 wt % (expressed in elemental form of the coloring agent(s)).

According to certain optional embodiments, the present invention can be practiced to color ceramic bodies made from MgO stabilized zirconia, yttria stabilized zirconia, or alumina toughened zirconia (ATZ). Regardless of the specific ceramic to be colored, a process can begin with ceramic powder, optionally containing a binder. This powder, or powder and binder combination, can be shaped by a suitable technique such as pressing or casting. Optionally, this rough shape can be fired in a manner which may add strength and/or remove binder material, but falls short of full densification. This rough shape may be in the form of a blank or block, but is not limited to any specific geometry. This rough shape can then be machined by any suitable technique such as a CAD/CAM technique of the type described herein. After shaping, the article is subsequently sintered to final density.

According to another embodiment, the present invention provides an atmosphere powder that stabilizes the color of an as-sintered article with respect to subsequent environments or processing conditions, such as porcelain firing and/or pressing conditions. This is achieved by adjusting the composition of the atmosphere powder such that the resultant oxygen activity sets the as-sintered oxygen vacancy concentration at a level comparable to the concentration realized for porcelain firing and/or pressing conditions. One way of achieving a desired oxygen vacancy concentration is by formulating the atmosphere powder such that it produces an atmosphere during sintering that enhances the hydrolytic stability of the as-fired ceramic. One way to achieve a desired oxygen vacancy concentration is by formulating the atmosphere powder out of an oxide that generates the necessary oxygen partial pressure. For example, the oxide $CaZrO_3$, is known to have a higher oxygen vapor pressure than $ZrO_2$. Consequently, a $CaZrO_3$ atmosphere powder would be expected to result in a sintered zirconia with lower oxygen vacancy concentration, versus if the atmosphere powder was $ZrO_2$. Another way to achieve a desired oxygen vacancy concentration is to blend together oxides which have different oxygen vapor pressures. For example, a blend of $CaZrO_3$ and $ZrO_2$ can be expected to have a vapor pressure in between that of pure $CaZrO_3$ and $ZrO_2$, and hence result in an oxygen vacancy concentration of the sintered zirconia that is in between that realized for $CaZrO_3$ and $ZrO_2$ atmosphere powder. A key restriction dictating selection of the atmosphere powder oxide is that it has higher melting point than the sintering temperature of the article to be sintered, i.e., a melting point greater than approximately 1500° C. Consequently, the oxygen vacancy concentration should not change during the porcelain firing/pressing conditions, thereby stabilizing color. The change in color can for example be quantified by comparing the CIE $L^*$, $a^*$, $b^*$ coordinates of ceramic article which has been overlayed with porcelain and then stripped of the porcelain overlay, to those of the as-fired ceramic article, where the change in color, $\Delta E$, is calculated according to the formula: $\Delta E=((L_s-L_{af})^2+(a_s-a_{af})^2+(b_s-b_{af})^2)^{1/2}$, where the subscripts s and af indicate the stripped and as-fired surfaces, respectively. According to certain embodiments, $\Delta E$ should be less than about 6. According to further embodiments, $\Delta E$ should be less than about 3.

According to another embodiment, the atmosphere powder can be formulated such that it produces an atmosphere during sintering that enhances the hydrolytic stability of the as-fired ceramic. By way of example, firing in an atmosphere that promotes the incorporation of aluminum into the ceramic enhances hydrolytic stability. Thus, according to certain embodiments of the present invention, the composition of the atmosphere powder can be formulated such that includes aluminum, or compounds thereof.

According to still another embodiment, the present invention can be practiced to ensure that ceramic bodies, for example, white zirconia, do not discolor during the sintering step due to coloring impurities within the furnace chamber. This is achieved at least in part by utilizing an atmosphere powder comprising no coloring agents as a protective barrier from the discoloring impurity and/or as a "getter" of said impurity.

According to alternative embodiments of the present invention, the article to be sintered can be formed or shaped by a number of alternative techniques including gel casting, slip casting, freeze casting, electrophoretic deposition, injection molding, or rapid prototyping (also known as solid freeform fabrication). "Rapid prototyping" is the generic term for net-shape manufacturing of materials into complex shapes and includes, stereolithography, photo-stereolithography, digital light processing (DLP), selective area laser deposition, selective laser sintering (SLS), electrophoretic deposition (EPD), robocasting, fused deposition modeling (FDM), laminated object manufacturing (LOM), or 3-D printing, as described in greater detail in U.S. Patent Application Publication No. 2005/0023710, which is incorporated hereby by reference.

A number of different dental articles are contemplated. For example, dental articles formed according to the principles of the present invention can include: supports or frameworks for a dental restorations; a coping; pontic; denture teeth; space maintainers; tooth replacement appliance; orthodontic retainer; denture; post jacket; facet; splint; cylinder; pin; connector; crowns; partial crowns; veneers; onlays; inlays; bridges; fixed partial dentures; Maryland Bridges; implant abutment; and whole implant.

Firing methods performed consistent with the principles of the present invention can be carried out by number of different techniques. By way of example, firing methods performed according to the present invention can be performed by either (i) burying the ceramic material to be colored in an atmosphere powder, (ii) covering the ceramic material to be colored in an atmosphere powder or (iii) placing the ceramic material to be colored in the vicinity of the powder within an open or closed enclosure. Any and all of the above techniques may involve firing the ceramic material to be colored and the atmosphere powder on a firing plate, or in a suitable enclosure (e.g., a crucible) that may optionally be covered or closed. Firing according to certain embodiments of the present invention may be performed using microwave heating techniques.

Figure 1:
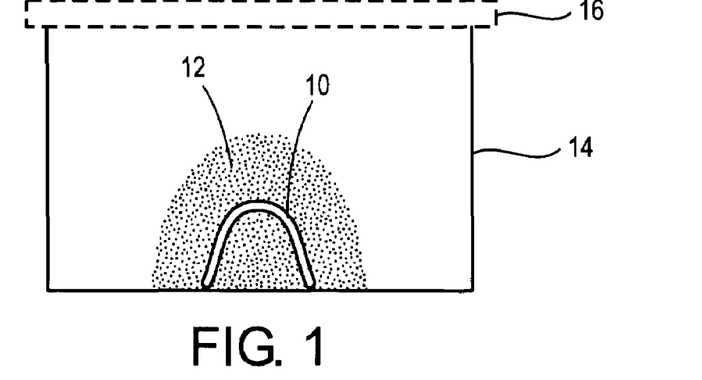
FIG. 1 is a schematic illustration of a sintering technique carried out according to a first aspect of the present invention.

An example of the first option is illustrated in FIG. 1. As illustrated therein, a ceramic material to be colored, which may optionally be in the form of a dental article such as a framework or prosthesis 10, is buried in a ceramic-based atmosphere powder 12 containing at least one coloring agent. As used herein, the term "buried" means that the amount of powder covering the article is such that the outline or outer periphery of the article is not perceptible or apparent. The atmosphere powder can be applied such that all or some of the surfaces of the article are in contact with the atmosphere powder 12. The framework or prosthesis 10 and the powder 12 are contained within a suitable container or enclosure such as crucible 14 during the firing procedure. A lid 16 may optionally be provided over the crucible 14 in order to promote diffusion of the at least one coloring agent into the dental framework or prosthesis 10 during the firing process.

Figure 2:
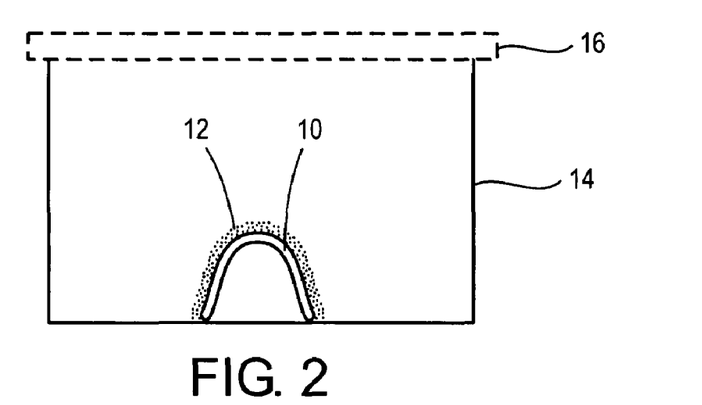
FIG. 2 is a schematic illustration of a sintering technique carried out according to a second aspect of the present invention.

FIG. 2 illustrates the second option mentioned above. As illustrated therein, a ceramic material to be colored, optionally a dental article in the form of the dental framework or prosthesis 10, is covered with a layer of ceramic-based atmosphere powder 12 containing at least one coloring agent. As used herein, "covered with a layer" means that the amount of powder covering the article is such that the outline or outer periphery of the article remains apparent or perceptible. The atmosphere powder may be applied in a manner such that some or all surfaces of the article are in contact with the atmosphere powder. The framework or prosthesis 10 and the powder 12 are contained within a suitable container or crucible 14 during the firing procedure. A lid 16 may optionally be provided over the crucible 14.

Figure 3:
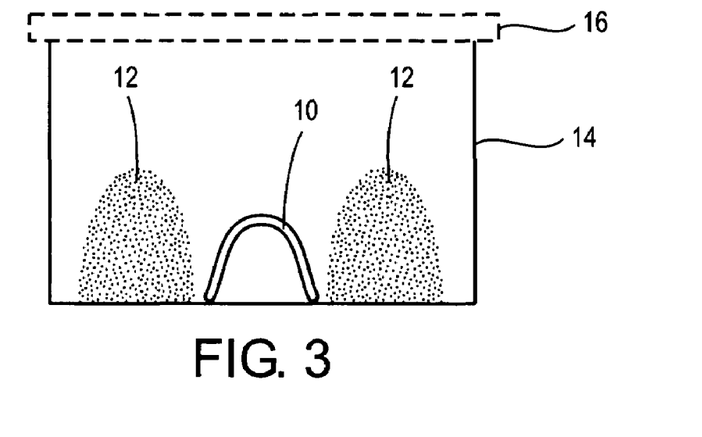
FIG. 3 is a schematic illustration of a sintering technique carried out according to a further aspect of the present invention.

FIG. 3 illustrates the third option mentioned above. Thus, as illustrated therein, the ceramic material to be colored, such as a dental article in the form of a dental framework or prosthesis 10 is placed within the container or closure, such as crucible 14, and the atmosphere powder 12 containing at least one coloring agent is provided adjacent to the dental framework or prosthesis 10, optionally in a manner which surrounds the same during the firing process. A lid 16 may optionally be provided on crucible 14.

The effect of the powder is to create an atmosphere of the at least one coloring agent, which then diffuses into the ceramic framework during sintering, thereby imparting color. Diffusion of the at least one coloring agent from the atmosphere powder to the machined body can be by one or a combination of mechanisms, such as solid-state, surface and vapor phase transport as in the case of options (i) and (ii), or exclusively by vapor phase transport, as for the case of option (iii). The shade that is imparted can be controlled by the combination/concentration(s) of the coloring agent(s) in the atmosphere powder (i.e., the chemical composition of the powder). The sintering temperature can be about 1150° C. to 1700° C. The ceramics emerge from the furnace, translucent, and colored. The sintered material also has good physical properties. For example, a colored sintered ceramic can be provided with a density of >99%, a grain size of about 0.2 to 1.5 μm, and an average flexural strength (3-pt-bend test performed according to ISO 6872: Dental Ceramics) in excess of 800 MPa. The shades achieved are suitable for overlaying with zirconia porcelain systems to achieve clinically relevant tooth-colored shades for the finished restoration.

Certain principles and advantages which can be associated with the present invention will now be further described by reference to specific embodiments in the following examples. It should be understood that these examples are illustrative of the principles of the present invention and not necessarily limiting the scope thereof. Test specimens were sintered in a model DT-31-SBL-9912-Y550-00 furnace (Deltech Inc., Denver, Colo.) which is $MoSi_2$ resistance heated furnace. Color was evaluated as necessary, both visually, by a certified dental technician, and measured on a white background using a ColorTec-PSM™ spectrophotometer from ColorTec™, Clinton, N.J. The color parameters were read in reference to D65/10° illuminations standard. Post-fired densities were measured by the Archimedes method.

EXAMPLE 1

8 mol % MgO stabilized zirconium oxide (MSZ-8, from Daiichi Kigenso Kagaku Kogyo Co. Ltd. Osaka, Japan) was blended with a $(V,Zr)O_2$ yellow baddeleyite pigment (C-464EZ from Ferro Corp., Washington, Pa.), in different ratios, as shown in Table 1. Presintered zirconia discs 27 mm dia×2.75 mm thick, made from commercial zirconia powder TZ-3YB-E, Tosoh Corp., were then placed on an alumina firing plate, and covered with the MSZ-8 and C-464EZ powder so as to cover the top and peripheral side surfaces of the disc (but not the bottom surface: e.g., FIG. 2). As used herein "presintered" refers to a body that has been partially fired in a manner to remove binder material, and optionally to at least partially densify the body to a point which is less than full densification. The ensemble was then fired, along with one "control" disc that was not covered, per the schedule: ambient to 1500° C. @ 4° C./m, 2 h hold; 1500° C. to ambient @ 4° C./m. The atmosphere powders were removed and the colors were recorded. Notably, only the disc surfaces that were in contact with the atmosphere powder became colored, with the other surface being white. These results are consistent with coloring being imparted by vanadium as derived from the C-464EZ powder. The results are shown in Table 1. They demonstrate that the atmosphere powder imparts a yellow color to the zirconia. Further, they show the yellow intensity can be controlled by the composition of the atmosphere powder, specifically the MSZ-8:C-464EZ ratio (i.e., ceramic powder:coloring agent ratio).

TABLE 1

|  | Blend 1 | Blend 2 | Blend 3 | Control |
|---|---|---|---|---|
| MSZ-8:C-464EZ- | 95:5 | 75:25 | 50:50 | n/a |
| Color | 89.65, | 80.81, | 77.99, | 90.75, |
| (CIE L, a, b)- | −6.20, | −2.61, | 2.02, | −1.05, |
|  | 26.23 | 51.10 | 59.17 | 5.45 |
| Color (visual)- | light yellow | dark yellow | darkest yellow | white |

EXAMPLE 2

MSZ-8 and C-464EZ powders, as described in example 1, were blended ratio of 95:5, by weight. A presintered zirconia disc, 27 mm dia×2.75 thick made from commercial zirconia powder TZ-3YB-E, Tosoh Corp., was buried (e.g., FIG. 1) in the 95:5 blend in an 7.8 cm dia.×2.7 tall alumina crucible, which was covered with an alumina lid prior to firing. The ensemble was then fired per the schedule: ambient to 1500° C. @ 4° C./m, 2 h hold; 1500° C. to ambient @ 4° C./m. The results are shown in Table 2 and demonstrate that highly dense zirconia parts that are light yellow on all surfaces can be achieved. These results are consistent with coloring being imparted by vanadium as derived from the C-464EZ powder.

TABLE 2

| Experiment: | Buried in coloring powder |
|---|---|
| Density: | 6.07 g/cc |
| Color (visual): | Yellow |
| Color (CIE L, a, b): | 86.59, −4.69, 26.89 |

EXAMPLE 3

MSZ-8 and C-464EZ powders were blended in the ratio 95:5, by weight. A presintered TZ-3YB-E (Tosoh Corp.) zirconia disc was placed in the center of a 7.8 cm dia.×2.7 tall crucible, the 95:5 blend was placed around its periphery (not contacting the disc; e.g., FIG. 3), and the crucible was covered with alumina lid prior to firing. The ensemble was then fired per the schedule: ambient to 1500° C. @ 4° C./m, 2 h hold; 1500° C. to ambient @ 4° C./m. The results are shown in Table 3 and demonstrate that highly dense zirconia parts that are yellow in color can be achieved by this technique on those surfaces that are exposed to the atmosphere powder. These results are consistent with coloring being imparted primarily by vanadium vapor as derived from the C-464EZ powder.

TABLE 3

| Experiment: | Coloring powder around periphery of sample |
|---|---|
| Density: | 6.07 g/cc |
| Color (visual): | Pale Yellow |
| Color (CIE L, a, b): | 87.55, −2.71, 13.92 |

EXAMPLE 4

TZP powder, TZ-3Y-E (Tosoh USA, Inc., Grove City, Ohio), is doped with 0 to 0.15 wt. % Pr(III) and Cr(III). This is done by creating a water-based slurry of the powder with the required amounts of Pr(III) acetate hydrate and Cr(III) chloride hexahydrate. The slurry is then dried and screened through a 200 mesh nylon sieve. The Pr, Cr content of the powder is chosen to yield a specific shade. A 3-unit-bridge, machined out of presintered TZ-3Y-E, is buried in the powder in an alumina crucible, which is covered with an alumina lid. The ensemble is fired per the schedule: ambient to 1500° C. @ 4° C./m, 2 h hold; 1500° C. to ambient @ 4° C./m. Result: A translucent 3-unit-bridge, with density of at least 6.05 g/cc, and of a shade suitable for overlaying with zirconia porcelain systems to achieve VITA shades A3, A3.5 and A4.

EXAMPLE 5

Fe-doped atmosphere powders of various concentrations (Table 4) were prepared by first dissolving the appropriate amount of Iron(III) chloride (anhydrous, 98%, Alfa Aesar) in distilled water, mixing the solution with TZ-3YB-E powder using a spatula (solution:zirconia=25:8, by weight), drying the wet powder, and finally screening through a 250 mesh (55 µm) screen. Presintered ~27 mm diameter×2 mm thick TZ-3YB-E zirconia discs were placed in an alumina crucible and covered with an ~2 mm thick layer of the respective atmosphere powders and sintered per the schedule: ambient to 1500° C. @ 4° C./m, 2 h hold; 1500° C. to ambient @ 4° C./m. The atmosphere powders were readily removed, revealing colored zirconia surfaces beneath. The surface coloration was remarkably uniform. Further, the colorations were restricted to an ~100 µm thick surface layer, beneath which the zirconia was white. The discs specimens were thinned from the white core side to a thickness of 0.5 mm and evaluated for color. The results are summarized in Table 4 showing that highly dense zirconia with yellowish to reddish-brown surface coloration can be achieved by this technique. Notably, powders 1 and 2, resulted in colors, a pale yellow and reddish-brown yellow, respectively, that were "tooth-like". More specifically, Experiments 1, and 2 resulted in as-sintered colors similar to that of Cercon® Base Colored (DeguDent GmbH), and VITA Coloring Liquid shade LL1 (VITA, Zahnfabrik H. Rauter GmbH & Co.), respectively. The latter were prepared per the manufacturers instructions and thinned to 0.5 mm thickness and then compared to the Fe-doped specimens.

TABLE 4

| Atmosphere Powder | | Sintered Sample | | |
|---|---|---|---|---|
| Powder # | Nominal Fe Concentration | Density (g/cc) | Color (visual) | Color (CIE L, a, b) |
| 1 | 0.27 wt. % | 6.10 | pale yellow "ivory" (similar to Cercon ® Base Colored) | 84.24, −1.17, 17.06 |
| 2 | 0.55 wt. % | 6.08 | Reddish-brown yellow (similar to Vita LL2) | 79.81, 0.77, 27.76 |
| 3 | 2.65 wt. % | 6.09 | Dark Reddish-Brown | 46.74, 16.74, 16.33 |

EXAMPLE 6

Atmosphere powders 1 and 3 from Table 4 were combined in several ratios, as given in Table 5, and blended for 15 minutes using a Retsch model MM2 mixer mill. These powders were subsequently used to color zirconia as per Example 5. The results are summarized in Table 5 showing that highly dense zirconia with yellowish to reddish-brown surface coloration can be achieved by this technique. As for Example 5, the surface coloration was remarkably uniform.

TABLE 5

| Atmosphere Powder | | Sintered Sample | | |
|---|---|---|---|---|
| Powder # | Ratio of Atmosphere Powder #1 to #3 | Density (g/cc) | Color (visual) | Color (CIE L, a, b) |
| 4 | 90:10 | 6.09 | Reddish-brown yellow | 80.34, 0.15, 26.10 |
| 5 | 80:20 | 6.08 | Light reddish-brown | 74.06, 5.04, 34.74 |
| 6 | 70:30 | 6.09 | Medium reddish-brown | 70.06, 8.96, 37.98 |

EXAMPLE 7

Using the laser scanner, D-250™ 3D Scanner, 3Shape A/S Copenhagen, Denmark, models of a single-unit and 3-unit-bridge preparations are scanned to create a 3D digital model which are saved as STL files. Using these files, the dental CAD software, DentalDesigner™, 3Shape A/S Copenhagen, Denmark is used to design the corresponding frameworks. The 3D models are saved as a STL files. These are transferred to a commercial CAM device with the ability to enlarge 3D digital model by the appropriate enlargement factor. Using an enlargement factor of approximately 1.243, which is inputted into the CAM software, presintered blocks are machined into an oversized single-unit and 3-unit-bridge frameworks. The as-machined frameworks are covered with powder #1 (Table 4) and sintered as per Example 5. The resultant sintered frameworks are of high density (approximately 6.05 g/cc), translucent, and uniformly colored with a shade similar to Cercon® Base Colored. The fit of the as-sintered frameworks onto the starting models is determined to be acceptable. This is indicative of isotropic shrinkage during the sintering step. The as-sintered frameworks are overlayed with Noritake Cerabien CZR Porcelain, Noritake Company, Inc., Fairlawn, N.J., to achieve a final VITA classic shade A2. The fit of the finished restorations to the starting models are determined to be acceptable. Shades and fit are evaluated by a certified dental technician.

EXAMPLE 8

The sintering furnace was run at a condition that corroded the protective silica layer off of the molybdenum disilicide heating elements. Presintered zirconia discs as per Example 1 were presintered, then sintered in the furnace as per the schedule of Example 1. The discs were in three configurations: (i) control (exposed, resting on an alumina firing plate), (ii) inside covered crucible, and (iii) buried in TZ-3YS zirconia powder inside a covered crucible. The crucibles were as per Example 2. The results are summarized in Table 6. It should be noted that for the case of a furnace with uncorroded, the control sinters to a white color. The results show that isolating the article to be sintered from the furnace chamber, by either putting in a covered crucible or buried in high-purity zirconia powder within a covered crucible, prevents discoloration.

TABLE 6

Results for sintering experiments conducted
in furnace with corroded heating elements.

| Experiment | Color of As-Sintered Disc |
| --- | --- |
| (i) Control (exposed): | Greenish yellow |
| (ii) inside covered crucible: | white |
| (iii) buried in zirconia powder in covered crucible: | white |

All numbers expressing quantities of ingredients, constituents, reaction conditions, and so forth used in the specification are to be understood as being modified in all instances by the term "about." Notwithstanding that the numerical ranges and parameters setting forth, the broad scope of the subject matter presented herein are approximations, the numerical values set forth are indicated as precisely as possible. Any numerical value, however, may inherently contain certain errors resulting, for example, from their respective measurement techniques, as evidenced by standard deviations therefrom.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A method of forming a dental article, the method comprising:
   (a) forming a body from a ceramic-containing powder;
   (b) shaping the body into a shape corresponding to the dental article; and
   (c) firing the shaped body in proximity to an atmosphere powder comprising at least one coloring agent;
   wherein the coloring agent diffuses into the shaped body during firing, imparting color to the shaped body.

2. The method of claim 1, wherein the body comprises a presintered block.

3. The method of claim 1, wherein the dental article comprises: a support or framework for a dental restoration; a coping; a pontic; denture teeth; space maintainers; a tooth replacement appliance; and orthodontic retainer; a denture; a post jacket; a facet; a splint; a cylinder; a pin; a connector; a crown; a partial crown; a veneer; and onlay; and inlay; a bridge; fixed partial dentures; a Maryland bridge; and implant abutment; or a whole implant.

4. The method of claim 1, wherein the ceramic comprises zirconia.

5. The method of claim 4, wherein the zirconia comprises MgO stabilized zirconia.

6. The method of claim 4, wherein the zirconia comprises yttria stabilized tetragonal zirconia or alumina toughened zirconia.

7. The method of claim 1, wherein the ceramic-containing powder comprises a binder.

8. The method of claim 1, wherein (a) comprises pressing or casting.

9. The method of claim 1, wherein (b) comprises CAD/CAM processing.

10. The method of claim 1, wherein (a) and (b) comprise at least one of: gel casting; slip casting; freeze casting; electrophoretic deposition; injection molding; rapid prototyping; compaction; extrusion; pressing; uniaxial pressing; cold isostatic pressing; centrifugal casting; gravity casting; pressure casting; or injection molding.

11. The method of claim 1, wherein (c) comprises: (i) burying the shaped body in the atmosphere powder, (ii) covering the shaped body with the atmosphere powder, or (iii) placing the shaped body adjacent to the powder.

12. The method of claim 11, wherein (c) further comprises firing the shaped body in an enclosure.

13. The method of claim 12, further comprising placing a lid on the enclosure prior to firing.

14. The method of claim 1, wherein the dental article has CIE L*, a*, b* color coordinates within the CIE L*, a*, b* color space region associated with tooth colors.

15. The method of claim 1, wherein the atmosphere powder is formulated such that the resultant oxygen activity sets the as-sintered oxygen vacancy concentration of the article at a level comparable to an oxygen vacancy concentration realized for subsequent processing conditions.

16. The method of claim 15, wherein the subsequent processing conditions comprise applying an overlay porcelain onto the dental article and firing at a temperature of about 750° C. to about 1065° C. in a vacuum of about 10-100 torr for up to about one hour.

17. The method of claim 16, wherein a resistance to color change is imparted by the atmosphere powder setting an oxygen vacancy concentration of the dental article to a level comparable to the concentration realized during firing of the overlay porcelain.

18. The method of claim 15, wherein a change in color of the dental article from the as-sintered condition relative to the color after subsequent processing, ΔE, is less than about 6, as measured by a CIE L*, a*, b* system.

19. The method of claim 18, wherein the change in color, ΔE, is less than about 3.

20. The method of claim 1, formulating the atmosphere powder such that the atmosphere powder produces an atmosphere during sintering that enhances the hydrolytic stability of the dental article.

21. The method of claim 20, wherein the atmosphere powder comprises aluminum, or compounds thereof.

22. The method of claim 1, wherein the at least one coloring agent comprises one or more elements or compounds selected from: (i) the lanthanide series, excluding synthetic or radioactive elements, (ii) groups 5 to 11 of the periodic table, excluding synthetic or radioactive elements, and (iii) Ti or Sc.

23. The method of claim 1, wherein the at least one coloring agent is present at a concentration of about 0.0001 to about 50 weight % of the atmosphere powder, as expressed in elemental form.

24. The method of claim 23, wherein the least one coloring agent is in oxide form.

25. The method of claim 1, wherein imparting color to the shaped body comprises: (i) solid state diffusion; (ii) surface transport; (iii) vapor-phase transport; or (iv) combinations thereof.

26. The method of claim 1, wherein the shaped body is fired at a temperature of about 1150° C. to about 1700° C.

27. The method of claim 1, wherein the firing is performed using microwave energy.

28. The method of claim 1, further comprising presintering prior to the firing of the body.

29. A method of forming a fully dense colored ceramic body, the method comprising:
   (a) forming a body from a ceramic-containing powder;
   (b) shaping the body into a desired shape; and (c) firing the shaped body in proximity to an atmosphere powder comprising at least one coloring agent;

wherein the coloring agent diffuses into the shaped body during firing, imparting color to the shaped body.

30. The method of claim 29, wherein the body comprises a presintered block.

31. The method of claim 29, wherein the at least one coloring agent comprises one or more elements or compounds selected from: (i) the lanthanide series excluding synthetic or radioactive elements, (ii) groups 5 to 11 of the periodic table, excluding synthetic or radioactive elements, and (iii) Ti or Sc.

32. The method of claim 31, wherein the at least one coloring agent is present at a concentration of about 0.0001 to about 50 weight % of the atmosphere powder, as expressed in elemental form.

33. The method of claim 32, wherein the least one coloring agent is present in oxide form.

34. The method of claim 29, wherein (a) and (b) comprise at least one of: gel casting; slip casting; freeze casting; electrophoretic deposition; injection molding; rapid prototyping; compaction; extrusion; pressing; uniaxial pressing; cold isostatic pressing; centrifugal casting; gravity casting; pressure casting; or injection molding.

35. The method of claim 29, wherein the shaped body is fired at a temperature of about 1150° C. to about 1700° C.

36. The method of claim 29, wherein the firing is performed using microwave energy.

37. The method of claim 29, wherein (c) comprises: (i) burying the shaped body in the atmosphere powder, (ii) covering the shaped body with the atmosphere powder, or (iii) placing the shaped body adjacent to the powder.

38. The method of claim 29, wherein imparting color to the shaped body comprises: (i) solid state diffusion; (ii) surface transport; (iii) vapor-phase transport; or (iv) combinations thereof.

39. The method of claim 29, wherein the atmosphere powder is formulated such that the resultant oxygen activity sets the as-sintered oxygen vacancy concentration at a level comparable to an oxygen vacancy concentration realized for subsequent processing conditions.

40. The method of claim 39, wherein the subsequent processing conditions comprise firing at a temperature of about 750° C. to about 1065°C. in a vacuum of about 10-100 torr for up to about one hour.

41. The method of claim 40, wherein a change in color of the ceramic body from the as-sintered condition relative to the color after subsequent processing, ΔE, is less than about 6, as measured by a CIE L*, a*, b* system.

42. The method of claim 41, wherein the change in color, ΔE, is less than about 3.

43. The method of claim 29, formulating the atmosphere powder such that the atmosphere powder produces an atmosphere during sintering that enhances the hydrolytic stability of the ceramic body.

44. The method of claim 43, wherein the atmosphere powder comprises aluminum, or compounds thereof.

45. A method of forming a fully dense ceramic body that lacks discoloration, the method comprising:
(a) forming a body from a ceramic-containing powder;
(b) shaping the body into a desired shape;
(c) placing the shaped body in a firing atmosphere containing at least one impurity that promote discoloration of the ceramic body;
(d) placing the ceramic body in proximity to an atmosphere powder; and (e) firing the shaped body in proximity to an atmosphere powder;
wherein the atmosphere powder acts as at least one of a barrier and a getter for the at least one impurity.

46. The method of claim 45, wherein the atmosphere powder does not contain a coloring agent.

47. The method of claim 45, wherein (d) comprises: (i) burying the shaped body in the atmosphere powder, (ii) covering the shaped body with the atmosphere powder, or (iii) placing the shaped body adjacent to the powder.

48. The method of claim 45, wherein the at least one impurity comprises at least one of molybdenum and molybdenum disilicide.

49. A method of forming a dental article, the method comprising:
(a) forming a body from a ceramic-containing powder;
(b) shaping the body into a shape corresponding to the dental article; and
(c) firing the shaped body in proximity to an atmosphere powder comprising at least one coloring agent;
wherein (b) comprises CAD/CAM processing.

50. A method of forming a dental article, the method comprising:
(a) forming a body from a ceramic-containing powder;
(b) shaping the body into a shape corresponding to the dental article; and
(c) firing the shaped body in proximity to an atmosphere powder comprising at least one coloring agent;
wherein the atmosphere powder is formulated such that the resultant oxygen activity sets the as-sintered oxygen vacancy concentration of the article at a level comparable to an oxygen vacancy concentration realized for subsequent processing conditions.

51. The method of claim 50, wherein the subsequent processing conditions comprise applying an overlay porcelain onto the dental article and firing at a temperature of about 750° C. to about 1065° C. in a vacuum of about 10-100 torr for up to about one hour.

52. The method of claim 51, wherein a resistance to color change is imparted by the atmosphere powder setting an oxygen vacancy concentration of the dental article to a level comparable to the concentration realized during firing of the overlay porcelain.

53. The method of claim 50, wherein a change in color of the dental article from the as-sintered condition relative to the color after subsequent processing, ΔE, is less than about 6, as measured by a CIE L*, a*, b* system.

54. The method of claim 53, wherein the change in color, ΔE, is less than about 3.

55. A method of forming a dental article, the method comprising:
(a) forming a body from a ceramic-containing powder;
(b) shaping the body into a shape corresponding to the dental article; and
(c) firing the shaped body in proximity to an atmosphere powder comprising at least one coloring agent;
wherein the atmosphere powder is formulated such that the atmosphere powder produces an atmosphere during sintering that enhances the hydrolytic stability of the dental article.

56. The method of claim 55, wherein the atmosphere powder comprises aluminum, or compounds thereof.

57. A method of forming a dental article, the method comprising:
(a) forming a body from a ceramic-containing powder;
(b) shaping the body into a shape corresponding to the dental article; and (c) firing the shaped body in proximity to an atmosphere powder comprising at least one coloring agent;

wherein (c) comprises: (i) burying the shaped body in the atmosphere powder, (ii) covering the shaped body with the atmosphere powder, or (iii) placing the shaped body adjacent to the powder; and wherein (c) further comprises firing the shaped body in an enclosure.

58. A method of forming a dental article, the method comprising:
- (a) forming a body from a ceramic-containing powder;
- (b) shaping the body into a shape corresponding to the dental article; and
- (c) firing the shaped body in proximity to an atmosphere powder comprising at least one coloring agent;
- wherein the at least one coloring agent comprises one or more elements or compounds selected from: (i) the lanthanide series, excluding synthetic or radioactive elements, (ii) groups 5 to 11 of the periodic table, excluding synthetic or radioactive elements, and (iii) Ti or Sc.

59. A method of forming a dental article, the method comprising:
- (a) forming a body from a ceramic-containing powder;
- (b) shaping the body into a shape corresponding to the dental article; and
- (c) firing the shaped body in proximity to an atmosphere powder comprising at least one coloring agent;
- wherein the at least one coloring agent is present at a concentration of about 0.0001 to about 50 weight % of the atmosphere powder, as expressed in elemental form; and
- wherein the least one coloring agent is in oxide form.

60. A method of forming a fully dense colored ceramic body, the method comprising:
- (a) forming a body from a ceramic-containing powder;
- (b) shaping the body into a desired shape; and
- (c) firing the shaped body in proximity to an atmosphere powder comprising at least one coloring agent;
- wherein the at least one coloring agent comprises one or more elements or compounds selected from: (i) the lanthanide series excluding synthetic or radioactive elements, (ii) groups 5 to 11 of the periodic table, excluding synthetic or radioactive elements, and (iii) Ti or Sc.

61. A method of forming a fully dense colored ceramic body, the method comprising:
- (a) forming a body from a ceramic-containing powder;
- (b) shaping the body into a desired shape; and
- (c) firing the shaped body in proximity to an atmosphere powder comprising at least one coloring agent;
- wherein the shaped body is fired at a temperature of about 1150° C. to about 1700° C.

62. A method of forming a fully dense colored ceramic body, the method comprising:
- (a) forming a body from a ceramic-containing powder;
- (b) shaping the body into a desired shape; and
- (c) firing the shaped body in proximity to an atmosphere powder comprising at least one coloring agent;
- wherein the atmosphere powder is formulated such that the resultant oxygen activity sets the as-sintered oxygen vacancy concentration at a level comparable to an oxygen vacancy concentration realized for subsequent processing conditions.

63. The method of claim 62, wherein the subsequent processing conditions comprise firing at a temperature of about 750° C. to about 1065° C. in a vacuum of about 10-100 torr for up to about one hour.

64. The method of claim 63, wherein a change in color of the ceramic body from the as-sintered condition relative to the color after subsequent processing, $\Delta E$, is less than about 6, as measured by a CIE L*, a*, b* system.

65. The method of claim 64, wherein the change in color, $\Delta E$, is less than about 3.

* * * * *